United States Patent [19]

Hofman et al.

[11] Patent Number: 4,710,571
[45] Date of Patent: Dec. 1, 1987

[54] 1H-IMIDAZOL-1-ETHANOL ESTERS

[75] Inventors: Petrus S. Hofman, Haarlem; David W. R. Hall, Rotterdam; Kapil D. Jaitly, GL Delft, all of Netherlands

[73] Assignee: Gist-Brocades N.V., Delft, Netherlands

[21] Appl. No.: 899,920

[22] Filed: Aug. 25, 1986

Related U.S. Application Data

[60] Continuation of Ser. No. 772,721, Sep. 4, 1986, abandoned, which is a division of Ser. No. 604,083, Apr. 26, 1984, Pat. No. 4,563,473.

[30]  Foreign Application Priority Data

May 3, 1983 [NL] Netherlands ............... 8301550

[51] Int. Cl.$^4$ ............... C07D 403/12; C07D 409/12
[52] U.S. Cl. ................... 544/216; 544/238; 544/333; 544/405; 546/278; 548/253; 548/255; 548/269; 548/336; 548/341
[58] Field of Search ............... 548/336, 253, 341, 269, 548/255; 546/278; 544/333, 405, 238, 216

[56]  References Cited

U.S. PATENT DOCUMENTS 3,531,494  9/1970  Adolphi et al. ............... 548/341 X Primary Examiner—Richard A. Schwartz
Attorney, Agent, or Firm—Bierman & Muserlian

[57]  ABSTRACT

Novel sebum synthesis inhibiting compositions comprising a sebum inhibiting effective amount of at least one compound selected from the group consisting of compounds of the formula

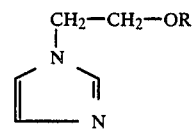

wherein R is selected from the group consisting of hydrogen and acyl of an organic carboxylic acid free of additional carboxyl group and their non-toxic, pharmaceutically acceptable acid addition salts and an inert pharmaceutical carrier and to a novel method of inhibiting sebum synthesis in warm-blooded animals and novel 1H-imidazol-1-ethanol esters.

9 Claims, No Drawings

1H-IMIDAZOL-1-ETHANOL ESTERS

PRIOR APPLICATION

This application is a continuation of U.S. patent application Ser. No. 772,721 filed Sept. 4, 1986, now abandoned, which in turn is a division of U.S. patent application Ser. No. 604,083 filed Apr. 26, 1984, now U.S. Pat. No. 4,563,473.

STATE OF THE ART 1H-imidazole-1-ethanol is a known compound and is described in British Pat. No. 939,681 and various other patents and patent applications relate to imidazole derivatives, including 1H-imidazole-1-ethanol esters such as French Pat. No. 1,486,817, German patent application Ser. No. 2509473 and European Pat. No. 19,359. In these, the esters are not specifically described but the acetate is known from J. A. C. S., Vol. 100 (11), p. 3575 (1978). Uses described for these compounds are insecticides, bitumen improvers, herbicides and intermediates but no therapeutic activity is mentioned.

OBJECTS OF THE INVENTION

It is an object of the invention to provide novel sebum inhibiting compositions and to a novel method of inhibiting sebum synthesis in warm-blooded animals.

It is a further object of the invention to provide novel esters of 1H-imidazole-1-ethanol.

These and other objects and advantages of the invention will become obvious from the following detailed description.

THE INVENTION

The novel sebum synthesis inhibiting compositions of the invention are comprised of a sebum inhibiting effective amount of at least one compound selected from the group consisting of compounds of the formula

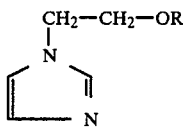

wherein R is selected from the group consisting of hydrogen and acyl of an organic carboxylic acid free of additional carboxyl group and their non-toxic, pharmaceutically acceptable acid addition salts and an inert pharmaceutical carrier.

Examples of organic carboxylic acids of R are alkane carboxylic acids of 1 to 18 carbon atoms such as acetic acid, propionic acid, butanoic acid, hexanoic acid and hexadecanoic acid; aromatic acids of 6 to 15 carbon atoms optionally substituted such as benzoic acid, p-toluic acid, p-nitrobenzoic acid; heterocyclic acids such as 4-pyridine-carboxylic acid, 2-thiophene carboxylic acid; cinnamic acid and retinoic acid.

Examples of suitable acids for the non-toxic, pharmaceutically acceptable acid addition salts are inorganic acids such as hydrochloric acid, hydrobromic acid, sulfuric acid, phosphoric acid and nitric acid and organic acids such as acetic acid, propionic acid, citric acid, oxalic acid, maleic acid, fumaric acid, glyoxylic acid, etc.

The compositions of the invention may be in the usual forms for toptical application such as lotions, gels, creams and sticks and in these preparations, 0.5–10% of active substance is preferably applied. The preparations may be prepared by methods commonly used in pharmacy. A lotion may, for instance, be obtained by dissolving the active substance in a mixture of water and 2-propanol or ethanol and mixing the solution obtained with a thickening agent such as hydroxypropylcellulose or an acrylic acid polymer (for instance Carbopol 940). In the end product, the amount of alcohol can vary from 10 to 80% and the amount of thickening agent depends upon the desired viscosity and may be for hydroxypropylcellulose 0.1–2% and for acrylic acid polymer 0.1–1%.

With a low alcohol content (<30%) also other thickening agents may be used, for instance hydroxethylcellulose, hydroxyethylmethylcellulose, hydroxypropylmethylcellulose, methylcellulose or sodium carboxymethylcellulose. Under certain conditions alginates, vegetable gums and starch derivatives are also useful as thickening agents. If desired, penetration promoting agents and/or humidity controlling agents may be used in the lotions such as isopropyl myristate, dioctyl sebacate, propylene glycol and glycerols in concentrations up to 10%.

A gel may be prepared by mixing an alcohol such as 2-propanol or ethanol with a gel forming agent and dissolving the active substance in the mixture. Suitable gel forming agents are polyacrylic acid (for instance 0.5–1.5% Carbopol 949, 934 or 941), hydroxypropylcellulose (for instance 2–3% Klucel HF), cellulose derivatives, alginate, vegetable gums and starch derivatives. The amount of alcohol may vary from 10 to 80%. Additional constituents may be added to the gel which may serve as penetration promoting agent and as weakening agent of the film remaining on the skin. Examples of such additives are: isopropyl myristate, ethyl lactate, dioctylsebacate, dioctyl phthalate, glyeryl triacetate, polyethylene glycol, propylene glycol, glycerol. These substances and many others with similar properties may be added in concentrations of 0.5–10% by weight.

A cream may be prepared by melting one or more fatty substances with an emulsifying agent and mixing the melt with a solution of the active substance in a mixture of water and an organic solvent and cooling the mixture obtained with thorough mixing at room temperature. As fatty substances may be applied, animal or synthetic fatty alcohols such as cetostearyl alcohol, liquid parafins, vegetable, animal, mineral and synthetic oils and fats and vegetable, animal and synthetic waxes. A suitable emulsifying agent is polyoxyethylenecetyl ether and other emulsifying agents or combinations thereof may be used, preferably from the group of nonionic emulsifying agents. Suitable organic solvents include propylene glycol, ethanol, isopropanol, butanediol-1,3, Solketal and glycerin formal.

Sticks may be prepared by mixing a solution of the active substance in a higher alcohol, for instance octyldodecanol, with a melt of waxy, oily substances and allowing the mixture to cool in molds. Examples of useful substances are waxy substances such as bees wax, cetyl palmitate, cetyl alcohol, Cutina LM, carnauba wax, candelilla wax, microcrystalline paraffin, cetostearyl alcohol, PCL-solid, stearic acid, palmitic acid, glycerin monostearate and yolk alcohols; oily substances: octyl dodecanol, isopropyl myristate and palmitate, ricinus oil, olive oil, Miglyol 812, oleyl alcohol, dioctyl sebactate, liquid paraffin. Also fatty substances as vaseline, theobroma oil and yolk may be used. Also some alcohols may be added which may serve as solvent for the active substance and/or penetration promoting agents, such as propylene glycol, butanediol-1,3 and hexylene glycol.

The pH of the preparations may be brought to the desired value (for instance 6) by addition of an organic or inorganic acid such as citric acid, tartaric acid, lactic acid, gluconic acid, hydrochloric acid and phosphoric acid. The percentages mentioned are always percents by weight in the end product.

The compositions of the invention show very good reversible local sebum synthesis inhibition. Since the compounds penetrate very well into the skin and mostly give little irritation, they are particularly suited for the therapeutic treatment of acne and seborrhea. The activity of the imidazole compositions is specifically directed to the sebum synthesis and they have no effect on lipid synthesis in organs other than the sebaceous glands. Up to now, no compositions were known with such a specific activity. There are sebum synthesis inhibitors for oral application such as cyproteron acetate and isotretinoin. The oral application is more prone to side effects than local application. Due to its anti-androgenic properties, cyproteron acetate is only used in women and isotretinoin has so many detrimental side effects that it is only used in very persistent, serious cases of acne. The new imidazole compositions of the invention are therefore an important therapeutic gain.

Esters of 1H-imidazole-1-ethanol with a great variety of acids have inhibited sebum synthesis. Compounds to be mentioned particularly as having a good activity are (a) esters of benzoic acid which may be substituted with lower alkyl or alkoxy or chlorine, bromine or iodine, particularly benzoic acid esters; (b) esters with phenylalkanecarboxylic acids in which the phenyl group may be substituted with lower alkyl or alkoxy or chlorine, bromine or iodine and in which the alkane part has at most 4 carbon atoms, particularly the benzenepropanoic acid esters; (c) esters with acids of the formula ACOOH in which A is sulfur, oxygen or nitrogen containing heterocyclic five- or six member ring, particularly 2-thiophenecarboxylic acid esters; and (d) esters with aliphatic carboxylic acids, particularly 2,2-dimethylpropanoic acid ester. The term "lower" is used to indicate alkyl or alkoxy with 1 to 6 carbon atoms.

2-(1H-imidazol-1-yl)-ethyl benzoate is particularly preferred as it gives in humans a good inhibition of the sebum secretion, a good penetration of the skin and little irriation. In animal tests, no lipid synthesis inhibition in other organs or hormonal activity were found.

The novel method of the invention for inhibiting sebum synthesis in warm-blooded animals, including humans, comprises administering to warm-blooded animals an amount of at least one compound of formula I to inhibit sebum synthesis. The compounds may be administered in any desired fashion but are preferably applied topically in the form of gels, creams, lotions and the like containing 0.5 to 10% by weight of the active ingredients.

The novel compounds of the invention are the carboxylic acid esters of formula I wherein R is an acyl of an organic carboxylic acid of more than two carbon atoms free of any other carboxyl groups. The said compounds may be prepared by reacting 1H-imidazole-1-ethanol with the acid halide of the desired carboxylic acid. The reaction is preferably effected by heating in an organic polar solvent such as acetonitrile, methyl isobutyl ketone or dioxane in the presence of an acid binding agent such as trimethylamine. The compounds may also be prepared by reacting imidazole with a compound of the formula $$X-CH_2-CH_2-OR \qquad II$$

wherein R has the above definition and X is a halogen.

In the following examples there are described several preferred embodiments to illustrate the invention. However, it should be uderstood that the invention is not intended to be limited to the specific embodiments. The structures of the compounds were confirmed by IR and NMR spectra.

EXAMPLE 1

11 g (0.05 mol) of 2,4-dichlorobenzyl chloride were added dropwise to a mixture of 5.5 g (0.05 mol) of 1H-imidazole-1-ethanol [prepared from imidazole and ethylene carbonate by the process of British Pat. No. 939,681], 20 ml of triethylamine and 150 ml of acetonitrile. The reaction mixture was kept at about 80° C. for another 1.5 hours and then the solvent was evaporated. The residue was dissolved in a mixture of ethyl acetate and diethyl ether and was then extracted with water and subsequently with dilute hydrochloric acid. The acidic aqueus layer was made alkaline after which the base was taken up in ethyl acetate. The organic layer was extracted three times with water, dried and partly concentrated by evaporation. The residue was acidified with maleic acid and the 2-(1H-imidazol-1-yl)-ethyl 2,4-dichlorobenzoate (Z)-2-butenedioate (1:1) obtained was crystallized from a mixture of 2-propanol, acetone and diethyl ether to obtain the product with a melting point of 116°–117° C.

With the aid of sodium bicarbonate, the free base was liberated from the salt and it had a melting point of 80.5° C.

EXAMPLE 2

Using the procedure of Example 1, the following compounds of formula I were prepared:

| $R_0$ | solvent | salt | Melting point (°C.) |
|---|---|---|---|
| 4-CF$_3$—C$_6$H$_4$—COO | acetonitrile | maleate | 106–107 |
| 4-Me—C$_6$H$_4$—COO | acetonitrile | maleate | 103–104 |
| 4-Me—C$_6$H$_4$—COO | acetonitrile | base[1] | oil |
| 4-tBu—C$_6$H$_4$—COO | acetonitrile | HCl | 104–105 |
| 4-tBu—C$_6$H$_4$—COO | acetonitrile | base[3] | oil |
| 4-Cl—C$_6$H$_4$—COO | acetonitrile | maleate | 137–138 |
| CH$_3$—COO | dioxane | base[2] | oil |
| C$_3$H$_7$—COO | dioxane | base[2] | oil |
| 4-MeO—C$_6$H$_4$—COO | acetonitrile | base[3] | oil |
| C$_6$H$_5$C$_2$H$_4$—COO | dioxane | base | ca. 30 |
| 4-C$_5$NH$_4$—COO | dioxane | ½oxalate[4] | 159–160 |
| C$_6$H$_5$CH=CH—COO | dioxane | base[5] | 109–110 |
| (CH$_3$)$_3$—COO | dioxane | base[2] | oil |

[1] via maleate
[2] purified with column chromatography (silica gel; ethyl acetate/methanol/triethylamine 100:40:1)
[3] via hydrochloride
[4] salt crystallzed from a mixture of methanol and ethanol
[5] crystallized from a mixture of methanol and acetone.

EXAMPLE 3

13.8 g (0.1 mol) of salicylic acid were added to a mixture of 80 ml of thionyl chloride and about 1 g of aluminum chloride at 30°–40° C. The mixture was then stirred at 45° C. for 2 hours and it was then concentrated by evaporation. The solution of the acid chloride obtained in 40 ml of dioxane was added dropwise to a mixture of 11.2 g (0.1 mol) of 1H-imidazole-1-ethanol, 40 ml of triethylamine and 50 ml of dioxane. The reaction mixture was refluxed for 1.5 hours and it was then concentrated by evaporation. The residue was dissolved in ethyl acetate and the solution was shaken with dilute hydrochloric acid. The acidic aqueous layer was made alkaline and the precipitated base was taken up in a mixture of diethyl ether and ethyl acetate The organic solution was then dried and concentrated by evaporation. Finally, the solid residue was crystallized from a mixture of toluene and petroleum ether (boiling range 28°–40° C.) to obtain 2-(1H-imidazol-1-yl)-ethyl 2-hydroxybenzoate with a melting point of 74°–75° C.

EXAMPLE 4

Using the procedure of Example 3, but with substitution of the salicylic acid by an equivalent of palmitic acid and conversion in acetone of the base obtained into the oxalate, 2-(1H-imidazol-1-yl)-ethyl hexadecanoate ethanedioate (1:1) with a melting point of 99°–100° C. was obtained.

EXAMPLE 5

A warm solution of 220 g (2.5 mol) of ethylene carbonate and 1 g of 4-toluene sulfonic acid in 200 ml of methyl isobutyl ketone (MIK) was added in about 60 minutes to a refluxing solution of 136 g (2 mol) of imidazole in 200 ml of MIK. The mixture was then refluxed for another 2 hours and after cooling, 300 ml of triethylamine were added. To the mixture obtained 280 g (231 ml 2 mol) of benzoyl chloride were subsequently added dropwise over 45 minutes at 40°–100° C. after which the mixture was stirred at 100°–110° C. for another 2 hours. Subsequently, the reaction mixture was cooled to about 10° C. The solid substance obtained was vacuum filtered and washed with 250 ml of MIK. The filtrate was concentrated by evaporation and the residue was dissolved in dichloromethane.

Successively, the solution was washed three times with water, dried, decolored with some silica gel, filtered and concentrated by evaporation to obtain 365 g of 2-(1H-imidazol-1-yl)-ethyl benzoate which without dilution were acidified with a warm saturated solution of maleic acid in acetone. After cooling to −10° C., the maleate was vacuum filtered and was washed with acetone and dried at about 80° C. in vacuo to obtain 365 g of product. The mother liquor was concentrated by evaporation and the residue was converted into the base, which subsequently was taken up in dichloromethane. The solution was washed, dried, decolored, filtered and concentrated by evaporation. The residue was converted again into 52 g of the maleate.

The combined portions of maleate were converted into the free base, which was taken up in dichloromethane, after which the solvent was evaporated again. The product had a melting point of 52°–53° C. and a boiling point of 174° at 0.5 mm Hg (67 Pa).

EXAMPLE 6

A mixture of 75 g of mandelic acid, 80 g of 2-chloroethanol, 100 ml of benzene, 100 ml of petroleum ether (60°–80° C.) and some p-toluene sulfonic acid was refluxed with removal of the water formed. After completion of the reaction, the mixture was concentrated by evaporation, after which the residue was taken up in diethyl ether. The ether solution was washed with alkaline water, dried and concentrated by evaporation. The chloro-ethyl ester of mandelic acid was obtained and a mixture of 0.1 mol of this ester and 0.2 ml of imidazole was heated for 5 min. at 130°–150° C. After cooling, water and diethyl ether were added to the mixture. The decanted ether layer was washed with water and then was extracted with dilute hydrochloric acid. Subsequently, the base was liberated from the acidic aqueous layer with the aid of dilute sodium hydroxide and was taken up in diethyl ether and converted into the oxalate. The latter finally was crystallized from a mixture of ethanol and diethyl ether to obtain 2-(1H-imidazol-1-yl)-ethyl α-hydroxybenzeneacetate ethanedioate (2:1) with a melting point of 131°–132° C.

EXAMPLE 7

Using the procedure of Example 3, 2-(1H-imidazol-1-yl)-ethyl 2-thiophenecarboxylate was obtained from 1H-imidazole-1-ethanol and 2-thiophenecarboxylic acid chloride in the form of an oil. The base was purified with the aid of column chromatography (silica gel, eluent dichloromethane/ethanol 95:5).

EXAMPLE 8

To a suspension of 12 g (0.04 mol) of retinoic acid (vitamin A acid) and 3.4 ml of pyridine in 160 ml of diethyl ether there were added dropwise at −5° C. 3.25 ml of thionyl chloride dissolved in 20 ml of diethyl ether. The mixture was stirred for another 2 hours at 0° C., after which it was filtered. The solid substance was washed with diethyl ether and the filtrate was then added dropwise at 0° C. to a solution of 5 g of 1H-imidazole-1-ethanol and 10 ml of triethylamine in about 100 ml of dioxane. The reaction mixture was stirred for another 2 hours at 20° C. and it was then filtered and concentrated by evaporation. The residue was taken up in dichloromethane, after which the organic solution was washed with water, with a solution of sodium bicarbonate in water and finally again with water and was dried and concentrated by evaporation. The solution of the base obtained in diethyl ether was acidified with oxalic acid in acetone and the precipitated salt was vacuum filtered and was washed with diethyl ether to obtain 2-(1H-imidazol-1-yl)-ethyl retinoate ethanedioate (2:1) as an amorphous substance.

EXAMPLE 9 (Lotion)

3 parts by weight of 2-(1H-imidazol-1-yl)-ethyl benzoate were dissolved in a mixture of 50 parts by weight of 2-propanol and 40 parts by weight of water and 0.5 part by weight of isopropyl myristate were added thereto. Then the liquid was thickened by addittion of 0.5 parts by weight of hydroxypropylcellulose and the pH was brought to 6 by addition of citric acid and the liquid was adjusted with water to 100 parts by weight.

EXAMPLE 10 (Gel)

1 part by weight of polyacrylic acid (Carbopol 940) was added to a mixture of 50 parts by weight of 2-propanol and 45 parts by weight of water and after complete dispersion, 2 parts by weight of 2-(1H-imidazol-1-yl)-ethyl benzoate were added under careful stirring and dissolved. The pH was brought to 6 with citric acid and water was added to obtain 100 parts by weight.

EXAMPLE 11 (Cream)

6 parts by weight of cetostearyl alcohol were melted at a temperature of about 70° C. with 2.5 parts by weight of polyoxyethylene cetyl ether (Cetamacrogol 1000) and 5 parts by weight of liquid paraffin. This liquid was combined with a solution of 2 parts by weight of 2-(1H-imidazol-1-yl)-ethyl benzoate in 10 parts by weight of propylene glycol and 74.5 parts by weight of water at 70° C. The liquids were cooled to room temperature with thorough mixing and the pH is brought to 6 with citric acid.

EXAMPLE 12 (Stick)

5 parts by weight of cetyl alcohol, 30 parts by weight of bees wax, 20 parts by weight of cetyl palmitate and 17 parts by weight of liquid paraffin were melted together and 3 parts by weight of 2-(1H-imidazol-1-yl)-ethyl benzoate were dissolved with gentle heating in 25 parts by weight of octyldodecanol. The two liquids were mixed with each other and the mixture was poured into molds and allowed to congeal at room temperature.

PHARMACOLOGICAL DATA

The sebum synthesis inhibiting activities of 1H-imidazole-1-ethanol and the esters of formula I were established in a number of animal species and particularly in the hamster much research has been carried out. Androgens administered to female hamsters stimulate the sebum synthesis in ear sebaceous glands and the extent of sebum synthesis is determined by incubating ear biopsies with radioactive acetate (Hall D. W. R. et al, Hormonal Control of Hamster Ear Sebaceous Gland Lipogenesis, Arch. Dermatol Res., 275, 1 (1983)). The test was based on the conversion of the added radioactive acetate into lipids which after extraction with hexane can be determined in a scintillation counter. In the following Table, the inhibition percentages of a number of substances are shown and the percentages may rise over 100%. A very strong activity of a compound will inhibit both the activity stimulated by androgen and the basal sebum synthesis activity of the sebaceous gland.

| R'* | salt/base | doses (μg per day) | lipid synthesis inhibition (%) |
|---|---|---|---|
| 2,4-Cl$_2$C$_6$H$_3$ | maleate | 100 | 37 |
| 2,4-Cl$_2$C$_6$H$_3$ | base | 100 | 60 |
| 4-ClC$_6$H$_4$ | maleate | 500 | 49 |
| 4-CF$_3$C$_6$H$_4$ | maleate | 500 | 70 |
| 4-tBuC$_6$H$_4$ | HCl | 500 | 81 |
| 4-tBuC$_6$H$_4$ | base | 100 | 67 |
| 4-CH$_3$C$_6$H$_4$ | maleate | 500 | 92 |
| 4-CH$_3$C$_6$H$_4$ | base | 100 | 91 |
| 4-CH$_3$OC$_6$H$_4$ | base | 100 | 83 |
| C$_6$H$_5$ | base | 100 | 82 |
| (CH$_2$)$_2$CH$_3$ | base | 100 | 106 |
| CH$_3$ | base | 100 | 82 |
| C$_6$H$_5$(CH$_2$)$_2$ | base | 100 | 76 |
| 4-pyridyl | oxalate | 100 | 44 |
| C$_6$H$_5$—CH=CH | base | 100 | 59 |
| (CH$_3$)$_3$—C— | base | 100 | 72 |
| CH$_3$(CH$_2$)$_{14}$— | oxalate | 100 | 44 |
| 2-thiophene | base | 100 | 89 |
| retinoic acid (=R'COOH) | oxalate | 100 | 39 |
| imidazolethanol | Maleate | 1000 | 37 |

*R'CO = R

Various modifications of the compositions and the method of the invention may be made without departing from the spirit or scope thereof and it is to be understood that the invention is intended to be limited only as defined in the appended claims.

What we claim is:

1. A compound selected from the group consisting of compounds of the formula

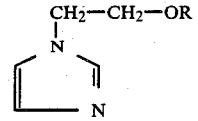

wherein R is an acyl of an organic carboxylic acid having at least 5 carbon atoms free of additional carboxyl groups selected from the group consisting of benzoyl optionally substituted with at least one member of the group consisting of alkyl and alkoxy of 1 to 6 carbon atoms, chlorine, bromine and iodine, phenylalkanoyl of 1 to 4 alkyl carbon atoms optionally substituted on the phenyl with at least one member of the group consisting of alkyl and alkoxy of 1 to 6 carbon atoms, chlorine, bromine and iodine,

and A is a 5- or 6-member aromatic heterocycle ring containing oxygen, nitrogen or sulfur, and acyl of an alkanoic acid of 5 to 18 carbon atoms and their non-toxic, pharmaceutically acceptable acid addition salts.

2. A compound of claim 1 wherein R is benzoyl optionally substituted with at least one member of the group consisting of alkyl and alkoxy of 1 to 6 carbon atoms, chlorine, bromine and iodine.

3. A compound of claim 1 wherein R is phenylalkanoyl of 1 to 4 alkyl carbon atoms optionally substituted on the phenyl with at least one member of the group consisting of alkyl and alkoxy of 1 to 6 carbon atoms, chlorine, bromine and iodine.

4. A compound of claim 1 wherein R is

and A is a 5- or 6-member aromatic heterocycle ring containing oxygen, nitrogen or sulfur.

5. A compound of claim 1 wherein R is an acyl of an alkanoic acid of 5 to 18 carbon atoms.

6. A compound of claim 1 selected from the group consisting of 2-(1H-imidazol-1-yl)-ethyl benzoate and its non-toxic, pharmaceutically acceptable acid addition salts.

7. A compound of claim 1 selected from the group consisting of 2-(1H-imidazol-1-yl)-ethyl benzenepropanoate and its non-toxic, pharmaceutically acceptable acid addition salts.

8. A compound of claim 1 selected from the group consisting of 2-(1H-imidazol-1-yl)-ethyl 2-thiophenecarboxylate and its non-toxic, pharmaceutically acceptable acid addition salts.

9. A compound of claim 1 selected from the group consisting of 2-(1H-imidazol-1-yl)-ethyl 2,2-dimethylpropanoate and its non-toxic, pharmaceutically acceptable acid addition salts.

* * * * *